United States Patent [19]

Bastida

[11] 4,281,285
[45] Jul. 28, 1981

[54] INSTRUMENT FOR MEASURING MOISTURE IN MATERIALS

[75] Inventor: Ezio M. Bastida, Milan, Italy

[73] Assignee: C.I.S.E. Centro Informazioni Studi Esperienze S.p.A., Italy

[21] Appl. No.: 88,976

[22] Filed: Oct. 29, 1979

[30] Foreign Application Priority Data

Oct. 31, 1978 [IT] Italy .............................. 29327 A/78

[51] Int. Cl.³ .......................................... G01R 27/04
[52] U.S. Cl. ............................................... 324/58.5 B
[58] Field of Search .............. 324/58.5 B, 58 B, 58 R

[56] References Cited

U.S. PATENT DOCUMENTS 3,162,807  12/1964  Alford ................................ 324/58 B
3,482,160  12/1969  Prine ................................. 324/58.5 B

*Primary Examiner*—Stanley T. Krawczewicz
*Attorney, Agent, or Firm*—Karl W. Flocks

[57] ABSTRACT

This invention relates to a new type of instrument for measuring the moisture in materials, particularly in earth and sand. According to the invention, the instrument comprises a constant amplitude microwave signal generator, a waveguide container for a sample of moist material, a microwave signal amplitude detector and a directional coupler of high directivity disposed between said generator, said container and said detector.

By means of said directional coupler the constant amplitude microwave signals are transmitted to the sample, which reflects to same, and reflected signals are transmitted to the detector.

4 Claims, 6 Drawing Figures

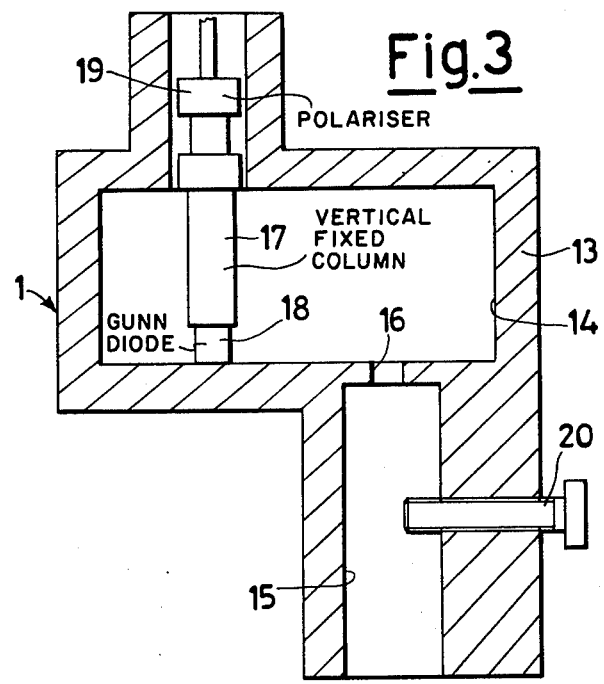
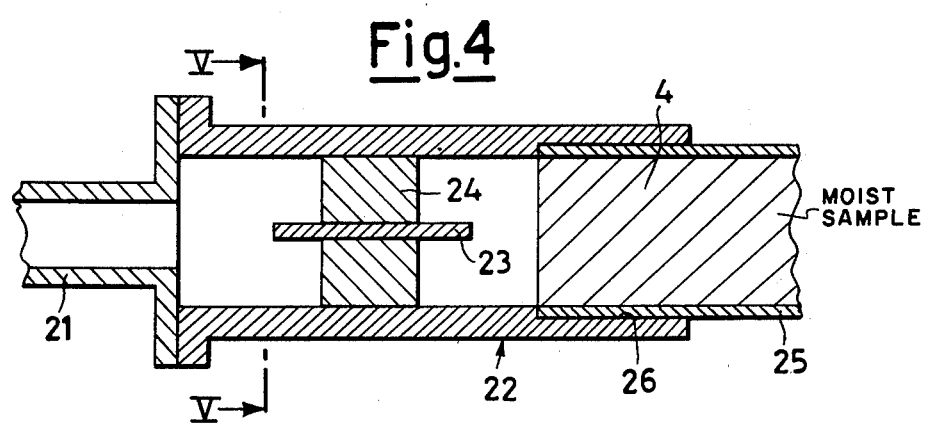
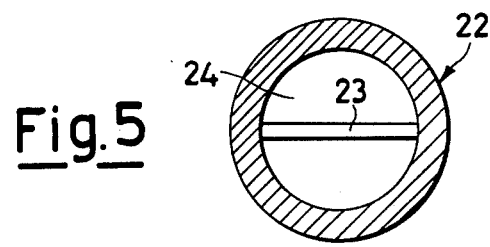

INSTRUMENT FOR MEASURING MOISTURE IN MATERIALS

This invention relates to a new type of instrument for measuring the moisture in materials, and is particularly suitable for measuring the moisture in earth and sand.

The problem of measuring the moisture content of bodies without substantially altering their physical and chemical properties is of great importance in modern scientific and industrial metrology.

The various methods used up to the present time for this type of measurement are based on radioactive and electrical techniques. With regard to the former, the accuracy obtainable is completely unsatisfactory, and their use is not recommended both because of their high cost and the considerable operational complication because of the presence of intense radiation and high energy.

With a few rare exceptions, which are however irrelevant because of the poor accuracy attained, instruments based on electrical techniques utilise radio or microwave frequency signals, and are based on absorption or resonance frequency measurements.

These two different electrical approaches are both unsuitable for measurements on particular types of material, such as earth. In this respect, resonance methods are hardly suitable for measurements on materials of high water content (in earth, this sometimes exceeds 70% of water by volume), while absorption methods give results which are too dependent on salt content (variable from one type of earth to another) and on temperature, and also require a sample of constant dimensions.

It would therefore be of considerable interest to provide a low-cost instrument which besides supplying a measurement which is independent of the type of earth, salt content, particle size and temperature, also enables a measurement to be made which, for obvious reasons of simplicity, is independent of the length of the sample, and is made by directly using the hollow cylindrical metal punches with which earth samples are normally withdrawn, both from the surface and at depth (cores). This constitutes the object of the present invention.

According to the invention, this object is attained, and in particular all the aforesaid requirements are satisfied, by means of an instrument comprising a constant amplitude microwave signal generator, a waveguide container for a sample of moist material to be examined, a microwave signal amplitude detector and a directional coupler of high directivity disposed between said generator, said container and said detector to transmit to the container the constant amplitude microwave signal generated by the generator and to transmit to the detector the microwave signal which is reflected by the sample contained in the container, and of which the amplitude varies with the humidity.

In other words, the instrument according to the invention is based on generating a constant amplitude microwave signal and feeding it to a moist sample contained in a waveguide of suitable shape, from which a microwave signal is reflected, the amplitude of which varies with the dielectric constant of the material of the sample, and thus with the moisture content thereof. The amplitude of the reflected signal is detected by the detector in the form of voltage, and after suitable analogue, numerical or simply manual processing, constitutes the measurement of the water content of the material under examination.

A measurement of this type obviously requires the generator to emit an absolutely constant power under the most variable operating conditions (temperature, atmospheric humidity, load etc.).

This can be attained either by manually adjusting the voltage applied to the active element of the generator before each set of measurements (if for example the oscillator is one in which the power depends on the supply voltage), or by using an automatic signal level control system in the case of more sophisticated apparatus. In this latter case, assuming that the generator is constituted by an oscillator of the aforesaid type, part of the signal generated by the oscillator is withdrawn upstream of the directional coupler and is detected by a further detector. The voltage detected by this further detector is then amplified and compared with a reference voltage in order to produce an error signal for supplying the oscillator.

It is advantageous if the signal generated by the generator has a very low harmonic content, as detectors are notoriously sensitive to signals of harmonic frequency, and indeed with which the circuit is not able to operate correctly.

The need for simple and effective automatic or non-automatic control of the generator power together with the need for controlling the harmonic frequency signal makes it particularly preferable to use a generator in the form of a particular Gunn diode oscillator which forms the subject matter of a simultaneously pending patent application by the applicant of the present application, and is substantially distinguished by the presence of an auxiliary cavity inaccessible to the fundamental frequency and provided with tuning means, which enables the load impedance seen by the Gunn diode at harmonic frequencies to be varied without in any manner influencing its behaviour at the fundamental frequency.

The use of this oscillator avoids costly circuits due to the need for dissipative filtering of the signal or the connection of active elements for automatically controlling the power level downstream of the resonant cavity and upstream of the detectors.

Giving a more detailed explanation, the need for a spectrally pure and stable signal makes it necessary to use a waveguide cavity which notably has a greater selectivity than coaxial cable or strip line cavities. However, waveguide cavities show strong fluctuations in the curves of output power against supply voltage of the Gunn diode. These fluctuations mean that as the supply voltage increases, the derivative of the power with respect to the voltage can change sign, so compromising the possibility of electronically controlling the oscillator power level by the voltage applied across the diode. As demonstrated in the article by E. M. Bastida entitled "Harmonic effects on the bias-tuning features of waveguide Gunn diode oscillators", Alta Frequenza No. 6, Vol. XLV (1976), by suitably varying the impedance seen by the diode at the harmonic frequencies, and in particular at the second harmonic frequency, it is possible to obtain power-voltage curves free from fluctuations. On the one hand, the absence of these fluctuations allows automatic control of the oscillator power level to be obtained, and on the other hand prevents rapid variations in the power content of the signals generated by the oscillator. The facility for providing controlled amplitude signals even at harmonic frequency is essential for the accuracy of the measurement, because of the high sensitivity of the detectors to signals of this type, and because of the considerable increase in cost and overall size connected with the use of waveguide harmonic filters. The necessary and sufficient condition for satisfying these necessary requirements is to be able to suitably vary the impedance seen by the diode at the harmonic frequencies without altering the impedance at the fundamental frequency. This is precisely what happens in the case of the aforesaid Gunn diode oscillator.

Finally, it is preferable to use a container for the moist sample which enables the measurement to be made directly in the metal punches used for sample-taking. This container, which is easy to construct at low cost, substantially comprises a circular waveguide coupled to a rectangular waveguide by way of sudden transition, and a lamina disposed radially in the circular guide. The punch is inserted downstream of the lamina by taking advantage of a change in the inner diameter of the circular guide. The purpose of the lamina is to prevent possible resonance due to the presence of any transverse component of the $TE_{11}$ mode or component transverse to the $TM_{01}$ mode of the circular guide, which can be excited either by inaccurate centering during assembly or by any non-uniformity of the sample.

The characteristics of the present invention will be more apparent by referring to the accompanying drawings given by way of example only, in which:

FIG. 3 is an example of a waveguide Gunn diode oscillator, which can be used as the microwave generator in the instrument according to the invention;

FIG. 4 is an axial section through an example of the moist sample container which can be used in the instrument according to the invention;

FIG. 5 is a cross-section through said container on the line V—V of FIG. 4; and

Figure 1:
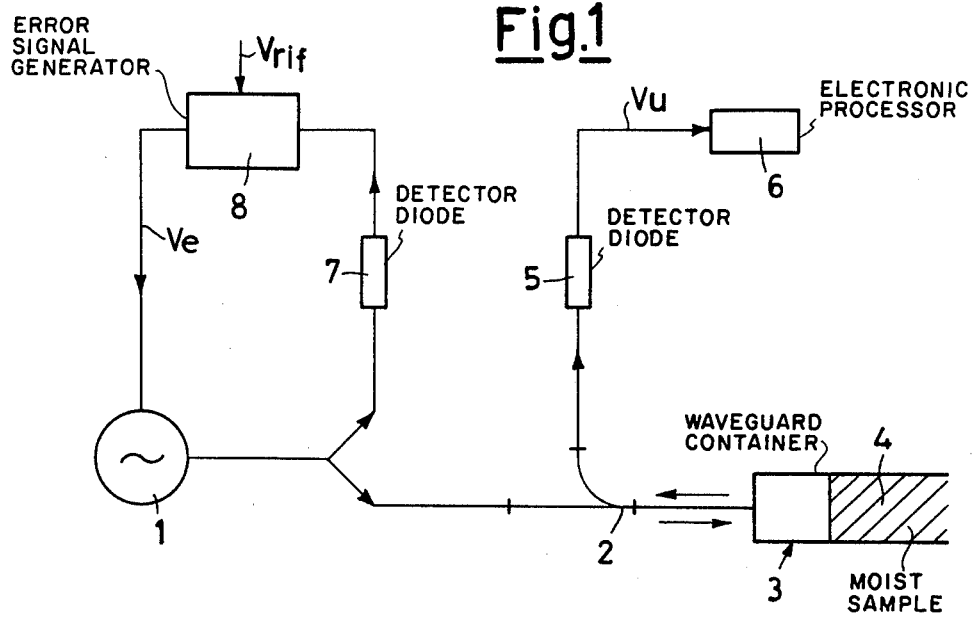
FIG. 1 is the basic schematic diagram of the instrument according to the invention.

The instrument shown diagrammatically in FIG. 1 comprises a constant amplitude microwave signal generator constituted by an oscillator 1, the power of which can be controlled by controlling the supply voltage. The signal generated by the oscillator 1 is fed through a directional coupler of high directivity 2 (for example a circulator) to a waveguide container 3 containing the moist sample 4 of which the moisture content is to be measured. Said moist sample generates a reflected signal, the amplitude of which depends on the dielectric constant of the sample examined and thus on its moisture content. The directional coupler 2 switches said reflected signal to a detector diode 5, which generates a voltage signal $V_u$ proportional to the amplitude of said reflected signal. A suitable electronic processor 6 finally converts the signal $V_u$ into the measured value of water content per unit of volume of the moist sample.

In order to provide the necessary constancy of the power delivered by the oscillator 1 under the various operating conditions (temperature, atmospheric humidity, load etc.), an automatic control system for the oscillator is provided, in which part of the generated signal is withdrawn upstream of the directional coupler 2 and is detected by a detector diode 7. The voltage across this latter is amplified and then compared with a reference voltage $V_{rif}$ in an error signal generator 8, from which an error signal $V_e$ leaves and is fed to the supply for the oscillator 1. A typical example of an error signal generator 8 is shown in FIG. 2, and comprises two amplifiers 9 and 10 for the reference voltage $V_{rif}$ and for the voltage detected by the detector diode 7, a differential amplifier 11 and an output amplifier 12 for controlling the oscillator 1.

The microwave generator preferably used is that shown in FIG. 3, which comprises a waveguide 13 with a rectangular main cavity 14, from which there branches laterally a cylindrical auxiliary cavity 15 communicating with the former by way of a restricted passage 16, which is of such dimensions as to allow the harmonic frequencies of the signal present in the main cavity to enter, but not the fundamental frequency. A Gunn diode 18 provided with a polariser 19 is disposed in the main cavity 14, between the base wall of the waveguide and a vertical fixed column 17. In the auxiliary cavity 15 there is disposed a harmonic tuning screw 20, which enables the reactance of the cavity 15 to the harmonic signal components to be varied, thus varying the load impedance seen by the Gunn diode at the harmonic frequencies without altering its behaviour at the fundamental frequency.

A particularly advantageous moist sample container is shown in FIGS. 4 and 5, which enables measurements to be made directly in the metal punches used for withdrawing the sample of moist material. As shown in FIGS. 5 and 4, said container comprises a waveguide of rectangular section 21 connected to the directional coupler 2, and a waveguide of circular section 22 coupled to the former by way of sudden transition. An absorbing lamina 23 provided with a dielectric support 24 is inserted into the circular guide 22 for the purpose of compensating the effects of discontinuity deriving from the sudden transition between the two waveguides. The punch 25 containing the sample of moist material 4 is inserted into the circular guide 22 downstream of the lamina 23, into a region of enlarged diameter 26 existing at the free end of the waveguide.

Figure 2:
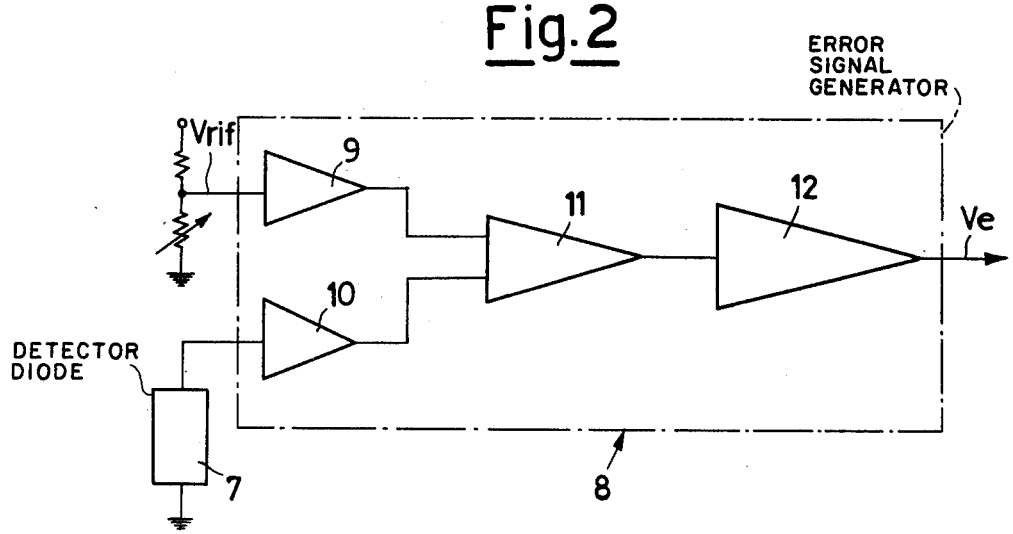
FIG. 2 is the schematic diagram of a typical automatic control system for the microwave generator included in the instrument according to the invention.
Figure 6:
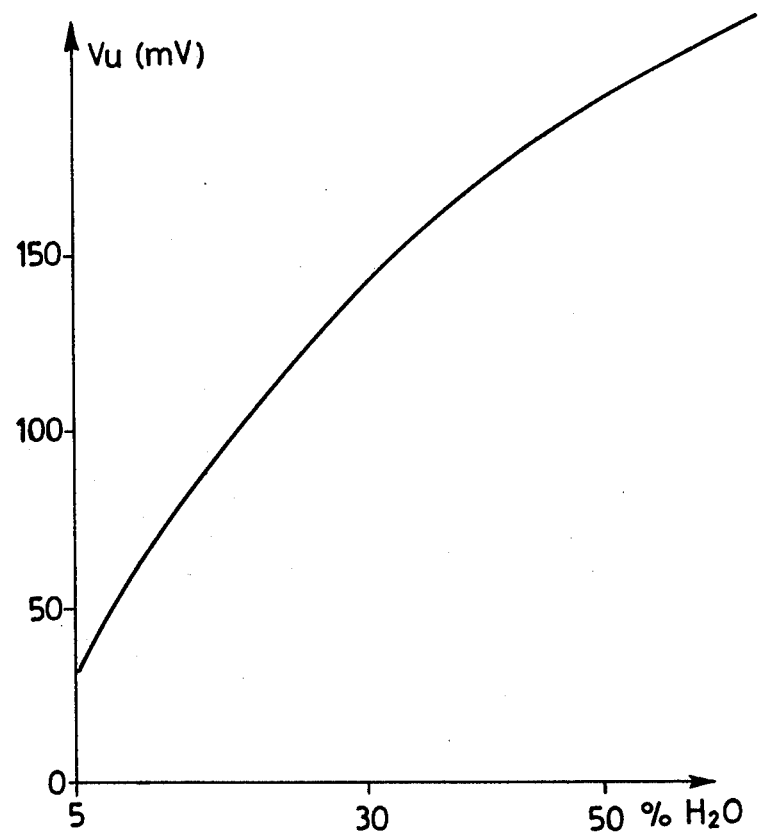
FIG. 6 shows a typical response curve for the instrument.

Experimental tests have shown that when constructed in practice with an oscillator 1 as shown in FIG. 3 (with a WR-90 waveguide), a control circuit as shown in FIG. 2, a container 3 as shown in FIGS. 4 and 5, a waveguide directional coupler 2 of the type known commercially by the symbol LTT AR2920, detector diodes 5 and 7 of HP 362A type and a T type Silver Lab PM 7275X waveguide for separating the part of the signal used for automatically controlling the oscillator, the instrument according to the invention is able to provide a response such as that represented by the graph of FIG. 6.

What I claim is

1. An instrument for measuring moisture in materials, comprising a constant amplitude microwave signal generator, a waveguide container for a sample of moist material to be examined, a microwave signal ampliutde detector and a directional coupler of high directivity disposed between said generator, said container and said detector to transmit to the container the constant amplitude microwave signal generated by the generator and to transmit to the detector the microwave signal which is reflected by the sample container in the container, and of which the amplitude varies with the humidity.

2. An instrument as claimed in claim 1, wherein said generator is constituted by an oscillator the power of which varies with its own supply voltage, there being provided an automatic control system for said oscillator which comprises means for withdrawing part of the signal generated by said oscillator and means for comparing said part of the signal with a reference signal in order to produce an error signal which is fed to the oscillator.

3. An instrument as claimed in claim 1, wherein said generator is constituted by a waveguide Gunn diode oscillator comprising a main cavity for housing the Gunn diode and an auxiliary cavity which is inaccessible to the fundamental component of the signal existing in the main cavity, and which houses harmonic tuning means arranged to produce any desired variation in the load impedance seen by the Gunn diode at the harmonic frequencies.

4. An instrument as claimed in claim 1, wherein said container comprises a waveguide of rectangular section connected by way of sudden transition to a waveguide of circular section which includes an absorbing lamina for compensating the effects of said transition and is provided with means for receiving a withdrawal punch for the sample of material to be measured.

* * * * *